United States Patent [19]

Barbucci et al.

[11] Patent Number: 4,944,767

[45] Date of Patent: Jul. 31, 1990

[54] SYNTHETIC MATERIAL APT TO STABLY ADSORB HIGH QUANTITIES OF HEPARIN, AND PROCESS FOR THE PRODUCTION THEREOF

[75] Inventors: Rolando Barbucci, Siena; Paolo Ferruti, Milan; Adalberto Grossi, Siena, all of Italy; Wilfried G. Lemm, Berlin, Fed. Rep. of Germany

[73] Assignee: G. Creamascoli S.p.A., Milan, Italy

[21] Appl. No.: 3,537

[22] Filed: Jan. 15, 1987

[30] Foreign Application Priority Data

Jan. 16, 1986 [IT] Italy ............................... 19094 A/86

[51] Int. Cl.$^5$ ............................... A61F 2/54
[52] U.S. Cl. ............................... 623/66; 623/1; 623/11; 106/124; 210/725; 514/56; 525/424; 525/459; 528/49; 528/60
[58] Field of Search ............... 106/124; 210/725, 735; 514/56; 525/424, 454, 459; 528/49, 60, 61; 623/1, 2, 11, 12, 66

[56] References Cited

U.S. PATENT DOCUMENTS

| | | | |
|---|---|---|---|
| 3,375,299 | 3/1968 | Levine et al. | 525/424 |
| 3,904,706 | 9/1975 | Hoeschele | 260/858 |
| 4,093,677 | 6/1978 | Ferruti et al. | 623/2 |
| 4,400,159 | 8/1983 | Orlowski et al. | 433/201.1 |
| 4,415,693 | 11/1983 | Chen et al. | 525/424 |
| 4,666,984 | 5/1987 | Carlick | 525/424 |

OTHER PUBLICATIONS

Basel, J. Appl. Physiol, "Experientia", vol. 29, pp. 93–95 (1973).
Ferruti et al., Journal of Polymer Science, "Synthesis and Properties of New Potentially Nonthrombogenic Polymeric Materials", vol. 15, pp. 2151–2162 (1977).
Martuscelli et al., Polymer, "Synthesis and Characterization of a Potentially Non-Thrombogenic Polyethylene-Poly(amido-amine) Graft Copolymer", vol. 19, p. 993 and pp. 1063–1066 (1978).
Ferruti et al., Biomaterials, "Heparin Adsorbing Capacities at Physiological pH of Three Poly(amido-amine) Resins, and of Poly(amido-amine)-Surface-Grafted Glass Microsphers", vol. 4, p146 and pp. 218–221 (1983).
Ferruti et al., Polymer, "Structural and Mechanical Properties of New Block Copolymers Designed for Biomedical Use", vol. 18, pp. 387–390 (1977).
Barbucci et al., Polymer, "Protonation Studies of Multifunctional Polymers with a Poly(amido-amine) Structure", vol. 19, pp. 1242 and 1329–1334 (1978).
Lyman et al., Intern. J. Polymeric Mater., "Polyurethane Elastomers in Surgery", vol. 5, pp. 211–229 (1977).

Primary Examiner—Richard J. Apley
Assistant Examiner—Paul Prebilic
Attorney, Agent, or Firm—Robbins & Laramie

[57] ABSTRACT

Synthetic material apt to stably adsorb high quantities of heparin, consisting of a polyurethane resin, crosslinked with copolymeric chains in correspondence of at least part of its own urethane groups $$-\underset{\underset{O}{\|}}{C}-NH-,$$

as per the following general formula:

$$\begin{array}{c} PU \\ | \\ N-\underset{\underset{O}{\|}}{C}-HN-R^3-NH-\underset{\underset{O}{\|}}{C}-N-R^2-N-R''-N-R^2- \\ | \qquad\qquad\qquad\qquad\qquad | \quad\; | \quad\; | \\ O=C \qquad\qquad\qquad\qquad\qquad R^1 \; R^1 \; R^1 \\ | \\ PU \end{array}$$

$$\begin{array}{c} \qquad\qquad\qquad\qquad\qquad\qquad\qquad\qquad PU \\ \qquad\qquad\qquad\qquad O \qquad\qquad\quad O \;\;| \\ \qquad\qquad\qquad\qquad \| \qquad\qquad\quad \| \;\;| \\ -N-C-HN-R^3-NH-C-N \\ | \qquad\qquad\qquad\qquad\qquad\quad | \\ R^1 \qquad\qquad\qquad\qquad\qquad\quad C=O \\ \qquad\qquad\qquad\qquad\qquad\qquad\quad | \\ \qquad\qquad\qquad\qquad\qquad\qquad\quad PU \end{array}$$

wherein,
  PU— is a polyurethanic polymeric chain,
  $R^1$ is an alkyl or aralkyl, containing functional groups inert to isocyanates,
  $R^2$ is an alkylene,
  $R^3$ is an alkylene, arylene or other bivalent organic radical, and
  $R''$ is a polyamidoaminic radical;
and process for the production of said material.

22 Claims, No Drawings

SYNTHETIC MATERIAL APT TO STABLY ADSORB HIGH QUANTITIES OF HEPARIN, AND PROCESS FOR THE PRODUCTION THEREOF

BACKGROUND OF THE INVENTION

1. Field of the Invention

The present invention relates to a new synthetic material apt to stably adsorb high quantities of heparin. Said material is therefore particularly suited for manufacturing protheses or other medical equipment, to which it confers remarkable non-thrombogenic properties when placed in contact with blood.

The invention also concerns a preferred process for the production of the aforementioned material, and the use of such material in manufacturing protheses and other medical equipment designed to come in contact with blood.

It is known that blood, in contact with the surface of prosthetic elements, generally determines the formation of blood clots. This at present constitutes the most serious factor limiting the use of synthetic materials (and particularly polymeric materials) in the field of protheses and artificial organs. The formation of blood clots may be chemically avoided by the systemic administration of anti-coagulants. The inadequacy of such a step is evident in the case of protheses designed to remain permanently in the organism, since, in this case, the entire circulatory system of the patient must be maintained in a modified condition, often for life. The above perhaps constitutes the main reason whereby it has not yet been possible to introduce an artificial heart in medical practice.

2. Description of the Prior Art

In order to reduce blood clot formation caused by polymeric material, a number of methods have been suggested; among these, the superficial heparinization of the above materials is undoubtedly one of the most important. Heparin is in fact endowed with marked anti-coagulant properties and is commonly used, in aqueous solution, as an anti-coagulant. It consists of a high charge-density acid mucopolysaccharide containing sulphonic, sulphamic and carboxylic groups. The aqueous solution behaves like a strong acid, and at a physiological pH, the substance is completely ionized. As mentioned above, it is known that heparin, bonded or in any case adsorbed by any type of material, is apt to confer to this latter non-thrombogenic properties.

The U.S. Pat. No. 3.865.723 hence describes basic polymers, obtained by polyaddition of bis-acrylamides with secondary diamines, apt to form stable complexes with heparin, but having mechanical properties of high rigidity and scarce moldability, which make them in practice unsuitable for use in the biomedical field.

Other similar polymeric materials have been described in Experientia 1973, 29, 93; Polymer 1977, 18, 378; J. Polym. Science 1977, 15, 2151; Polymer 1978, 19, 1063; Biomaterials 1983, 4, 218; Italian Patent application No. 20968 A/84 filed on May 17, 1984.

Of particular interest are polymers based on poly(amidoamine)s (PAA), which are apt to form stable complexes with heparin in an aqueous medium; such a property is maintained also when the PAA are inserted as segments in block copolymers with other types of polymers—e.g. polyethylene and polystyrene—or are grafted onto the surface of various materials, as glass, Dacron, etc.

Recent studies have finally been made on the possibility of associating PAA with polyurethanes. Said association in fact appears to be particularly advantageous, as it would allow to combine the easy heparinization properties of PAA with the satisfactory mechanical characteristics of polyurethanes, which have placed these materials among those most frequently used as components for equipment designed to come in contact with blood; e.g. vascular protheses, blood filters, catheters, cardiac valves, etc.

A first proposed method for obtaining said association consists in reacting first macrodiols with an excess of diisocyanate, thereby obtaining a polyurethane with reactive diisocyanate branches, onto which the PAA are subsequently grafted. A second method consists instead in carrying out a chemical etching directly onto a polyurethane prothesis, grafting thereon first the diisocyanate and subsequently the PAA.

Nevertheless, neither of said methods have given satisfactory results. In fact, in the first case, the reaction of copolymerization is not easy to control, whereby the product obtained does not provide sufficiently constant and reproducible chemical-physical characteristics, to allow a practical application thereof. The second method does not have this drawback, but the chemical etching of the grafting onto the polyurethane prosthetic element deteriorates, at times even considerably, its mechanical characteristics. In either case, there is anyhow a relative incompatibility with blood, which is essentially determined by the presence of a still insufficient number of active centres capable of stably bonding heparin.

SUMMARY OF THE INVENTION

The object of the present invention is therefore to supply a new synthetic material, providing the same satisfactory mechanical characteristics of polyurethane and being furthermore heparinizable to a considerable extent, and thus endowed with marked non-thrombogenic properties when placed in contact with blood.

A further object of the invention is to supply a particularly simple and efficient process for producing the aforementioned material.

According to the present invention, said objects are reached through a synthetic material consisting of a polyurethane resin, cross-linked with copolymeric chains in correspondence of at least part of its own urethane groups

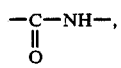

as per the following general formula:

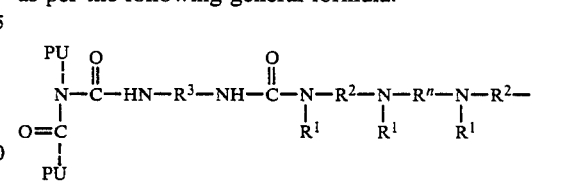

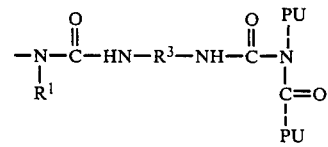

wherein,
PU—is a polyurethane polymeric chain;
R¹ is an alkyl or aralkyl, containing functional groups inert to isocyanates;

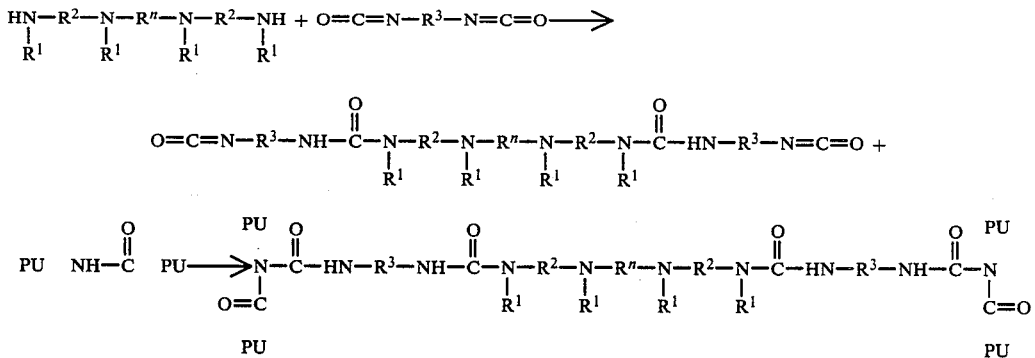

R² is an alkylene;
R³ is an alkylene, arylene or other bivalent organic residue of a diisocyanate; and
$R^n$ is a polyamidoaminic radical.

The aforespecified material is preferably produced with a process comprising the following steps:
(a) Preparing a solution of a poly(amidoamine) of general formula:

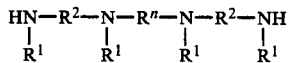

wherein, R¹ is an alkyl or aralkyl, containing functional groups inert to isocyanates; R² is an alkylene; and $R^n$ is a polyamidoaminic radical
with a diisocyanate of general formula:

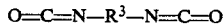

wherein, R³ is an alkylene, arylene, or other bivalent organic radical; in a first anhydrous solvent;
(b) Preparing a solution of a polyurethane in a second anhydrous solvent;
(c) Thoroughly mixing the solutions obtained in (a) and (b);
(d) Desiccating the solution obtained in (c).

DESCRIPTION OF THE PREFERRED EMBODIMENTS

It has in fact been found that, by mixing
(a) a solution of PAA with secondary amino end groups—easily obtainable with methods known in literature—and of suitable diisocyanates (e.g. hexamethylenediisocyanate, toluenediisocyanate, and the like), in anhydrous solvents such as $CHCl_3$, $CH_2Cl_2$, DMSO; with
(b) a polyurethane solution in anhydrous dimethylformamide (or dimethylacetamide, or hexamethylphosphoramide), one obtains solutions which, by elimination of the solvent, give rise to new materials having the characteristics of cross-linked block copolymers—in which the polyurethanic chains are interconnected with poly(amidoamine) chains—endowed with excellent mechanical properties similar to those of the starting polyurethane, and capable, at the same time, of stably adsorbing quantities of heparin even hundred times superior to those obtained with known materials, thereby assuming excellent nonthrombogenic properties.

The reactions which occur, operating in accordance with the invention, can be so represented:

wherein,
PU—represents a generic polyurethanic chain, of which only one functional group is evidenced;
R¹ is an alkyl or aralkyl, containing functional groups inert to isocyanates;
R² is an alkylene;
R³ is an alkylene, arylene or other bivalent organic residue of a diisocyanate; and
$R^n$ is a polyamidoaminic radical.

The reciprocal quantities of the two main components of the system, polyurethane and poly(amidoamine), are easily adjustable by varying their proportion in the reaction mixture, and the cross-linking of the end-product may be graded by varying the quantity of diisocyanate.

The preferred values of the molar ratio between polyurethane and poly(amidoamine) are included between 100:1 and 1:1, while those of diisocyanate in respect of PAA are between 0.75:1 and 5:1. If the quantity of isocyanic groups is greatly in excess in respect of the quantity of amine groups of the PAA, even direct cross-linking between polyurethanic chains could be obtained. After elimination of the solvents and desiccation, the new product appears as an elastic and flexible material. At this point, it is totally insoluble in any type of solvent, and particularly in water.

Heparin adsorption tests have been carried out on samples of the materials obtained. The quantity of heparin which can be adsorbed superificially, and is not dilutable except with drastic methods, as for example with NaOH 0.1M, is very high, i.e. from 10 to 100 times higher than that which can be adsorbed with all the other known materials apt to be haparinized. The invention will anyhow be better explained in the following examples, which should however not be considered as limiting the same.

EXAMPLE 1

0.65 g of hexamethylenediisocyanate were added to 10 ml of a 6% by weight solution in $CHCl_3$ (anhydrous solvent) of a PAA having the following formula:

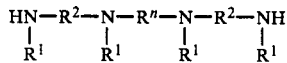

wherein, $$R^n = -\left[ CH_2CH_2-\overset{O}{\underset{\|}{C}}-N\diagup\diagdown N-\overset{O}{\underset{\|}{C}}-CH_2CH_2-\underset{R^1}{N}-R^2-\underset{R^1}{N} \right]_n CH_2CH_2-\overset{O}{\underset{\|}{C}}-N\diagup\diagdown N-\overset{O}{\underset{\|}{C}}-CH_2CH_2-$$

and, $R^1 = -CH_3$; $R_2 = -(CH_2)_4-$ having amino end groups and an average numeric molecular weight equal to about 15,000, obtained according to the descriptions in literature (P. Ferruti et al., J. Polym. Sci. Polym. Chem. Edn. 1977, 15, 2151; Polymer 1977, 18, 387; E. Martuscelli et al., Polymer 1978, 19, 1329).

To the solution were added 10 ml of a 10% solution of a commercial polyurethane (Pellethane 2363-80A) sold by Upjohn Polymers of Hertogenbosh Holland, in DMF. After homogenizing, the solution was subjected to vacuum in a room temperature desiccator, until the solvent was completely eliminated.

The resulting product appeared in the form of a resistent and flexible material, with properties similar to those of the starting polyurethane.

The quantity of basic nitrogen atoms corresponded exactly to that foreseen on the basis of the PAA quantity used. These were determined by immersion in an excess titrated acid solution and subsequently by acidometric titration of the residual acid. During this process, no passage of soluble material in solution was observed. The absence of free NCO groups was observed.

EXAMPLE 2

The same procedure was followed as in the previous example; however, Pellethane 2363-80A was substituted by a polyurethane especially prepared according to the teachings of D. J. Lyman et al. (International Journal Polymer Materials 1977, 5, 211).

The resulting product presented similar analytical data for what concerns the PAA content, the absence of extractable material and the absence of free NCO groups. Its mechanical properties were also similar to those of the starting polyurethane.

EXAMPLES 3-7

Using the same polyurethane of Example 1 (10% solution in DMF), the same PAA (6% solution in CHCl$_3$ anhydrous solvent) and hexamethylenediisocyanate in variable proportions, and proceeding as described above, one obtained the materials indicated in Table 1, wherein:

the second column (PU) indicates the quantity of the polyurethane solution (in ml);

the third column (PAA) indicates the quantity of the PAA solution (in ml);

the fourth column (DIISO) indicates the quantity of the diisocyanate (in g).

TABLE 1

| EX. | PU | PAA | DIISO |
|---|---|---|---|
| 3 | 10 | 2 | 0.3 |
| 4 | 10 | 12 | 1.5 |
| 5 | 10 | 12 | 2.5 |
| 6 | 10 | 6 | 1 |
| 7 | 10 | 0.5 | 0.1 |

In each case, the tests revealed a quantity of amino groups corresponding to the PAA quantity used, the absence of free NCO groups and the absence of extractable material.

EXAMPLES 8-10

The procedure was the same as in the previous Examples, using however the synthetic polyurethane mentioned in Example 2 (10% solution in DMF), again the PAA of the previous Examples (6% solution in CHCL$_3$ anhydrous) solvent), and hexamethylenediisocyanate. The materials indicated in the following Table 2, were obtained. (The indications correspond to those of Examples 3-7).

TABLE 2

| ES. | PU | PAA | DIISO |
|---|---|---|---|
| 8 | 10 | 5 | 0.5 |
| 9 | 10 | 15 | 1.2 |
| 10 | 10 | 1 | 0.15 |

Again, in this case, the tests revealed a quantity of amino groups corresponding to that of the PAA used, and the absence of free NCO groups and of extractable material.

EXAMPLE 11

A film of the product obtained according to Example 1, having a thickness of 0.5 mm and a surface of 5×5 cm, was immersed in a 0.5% solution of heparin in H$_2$O/C$_2$H$_5$OH/CH$_3$COOH, 48.5/48.5/5.3 in volume, for 24 hours. After this time, the film was repeatedly washed in a phosphate buffer solution (pH 7.4) until no heparin remained in the water used for washing. The heparin stably adsorbed in the material was then extracted using a NaOH solution 0.1M, and was determined quantitatively by means of standard biological tests. The heparin extracted with soda amounted to 25 mg, corresponding to $500.10^{-3}$ mg/cm$^2$.

Identical results were obtained with the materials mentioned in Examples 2-10.

By way of comparison, the quantities of heparin adsorbed by known heparinizable materials are reported hereunder:

| polyvinylchloride | $1.5 \cdot 10^{-3}$ mg/cm$^2$ |
|---|---|
| Glass (Balls having a diameter of 0.05 mm) | $2.5 \cdot 10^{-3}$ mg/cm$^2$ |
| Dacron | $2.5 \cdot 10^{-3}$ mg/cm$^2$ |
| Polyurethanes up to a maximum of | $50.0 \cdot 10^{-3}$ mg/cm$^2$ |

EXAMPLES 12-15

Still with the same starting products of Example 1, further materials according to the invention were prepared by varying this time merely the quantity of polyurethane, while the quantities of PAA and of hexamethylenediisocianate remained constant. The materials indicated in the following Table 3 were obtained. For these materials, in addition to the tests carried out for the materials of Examples 1 to 10 which confirmed the previous results, also the basic nitrogen content and the heparin content (Table 4), as well as some more interesting mechanical properties (Table 5), were determined. By way of comparison, we are also reporting hereunder (Example 15) the data of a polyurethane grafted by chemical etching, first with diisocyanate and subsequently with PAA, according to one of the known methods discussed further above.

TABLE 3

| Ex. | PU g | PAA g | PAA mmol | DIISO ml | DIISO mmol |
|---|---|---|---|---|---|
| 12 | 1.0 | 0.4 | 1.3 | 0.21 | 1.3 |
| 13 | 2.0 | 0.4 | 1.3 | 0.21 | 1.3 |
| 14 | 5.0 | 0.4 | 1.3 | 0.21 | 1.3 |

TABLE 4

| Ex. | BASIC NITROGEN FOUND μmol/cm² | HEPARIN FOUND mg/cm² |
|---|---|---|
| 12 | 6.1 | 0.286 |
| 13 | 3.2 | 0.014 |
| 14 | 1.1 | 0.007 |
| 15 | 0.2 | 0.006 |

TABLE 5

MECHANICAL PROPERTIES

| Ex. | Young's modulus (MPa) | ultimate tensile strength (MPa) | elongation at failure (%) | hysteresis at 50% elongation (%) | permanent set after 50% elongation (%) |
|---|---|---|---|---|---|
| 12 | 37 | 16.0 | 280 | 50 | 10 |
| 13 | 46 | 18.0 | 340 | 58 | 8 |
| 13 | 16 | 17.2 | 480 | 32 | 7 |
| 15 | 15 | 22.0 | 400 | 23 | 3 |

I claim:

1. Synthetic material apt to stably adsorb high quantities of heparin, characterized in that said synthetic material consists of a polyurethane resin, cross-linked with copolymeric chains in correspondence of at least part of the urethane groups

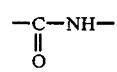

of said resin, as per the following general formula:

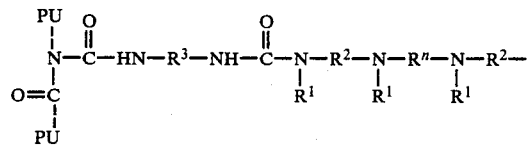

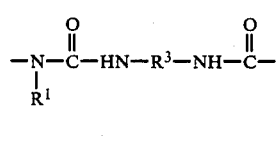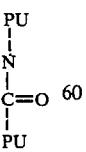

wherein,
PU—is a polyurethanic polymeric chain;
R¹ is an alkyl or aralkyl, containing functional groups inert to isocyanates;
R² is an alkylene;
R³ is an alkylene, arylene or other bivalent organic residue of a diisocyanate; and
Rⁿ is a polyamidoaminic radical.

2. The synthetic material of claim 1, wherein the cross-linking copolymeric chains only the following general formula:

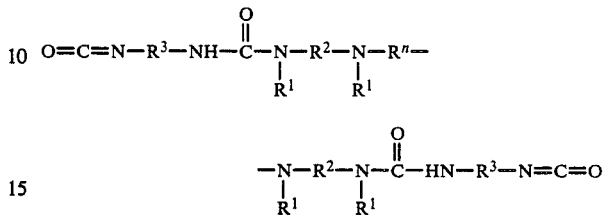

and are obtained by reaction between a poly(amidoamine) of general formula:

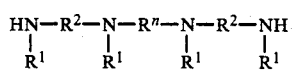

and a diisocyanate of general formula:

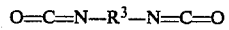

wherein R¹, R², R³ and Rⁿ are as defined in claim 1.

3. The synthetic material of claim 1, wherein Rⁿ has the following general formula:

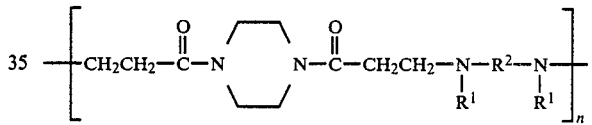

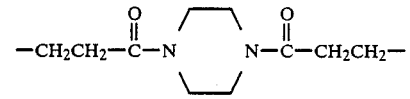

wherein R¹ and R² are as defined in claim 1.

4. The synthetic material of claim 1 and n is at least one but low enough that the poly (amidoamine) precursor is soluble in an anhydrous organic solvent, wherein:

R¹=—CH₃, R²=—(CH₂)₄—, R³=—(CH₂)₆—.

5. The synthetic material of claim 2 wherein Rⁿ has the following formula:

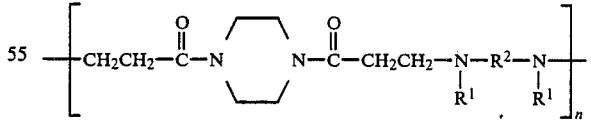

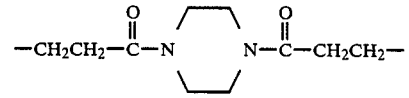

wherein R¹ and R² are as defined in claim 2 and n is at least one but low enough that the poly (amidoamine) precursor is soluble in an anhydrous organic solvent.

6. The synthetic material of claim 5, wherein R¹ is —CH₃, R² is —(CH₂)₄— and R³ is —(CH₂)₆—.

7. The synthetic material of claim 3 wherein $R^1$ is —$CH_3$, $R^2$ is —$(CH_2)_4$— and $R^3$ is —$(CH_2)_6$—.

8. The synthetic material of claim 1 which has superficially adsorbed some heparin.

9. The method of using of the material of claim 8, for manufacturing prosthetic elements or other materials equipment designed to come in contact with blood.

10. Process for the production of a synthetic material apt to stably adsorb high quantities of heparin, characterized in that said process comprises the following steps:

(a) Preparing a solution of poly(amidoamine) of general formula:

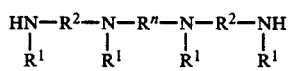

wherein, $R^1$ is an alkyl or aralkyl, containing functional groups inert to isocyanates; $R^2$ is an alkylene; and $R^n$ is a polyamidoaminic radical,
with a diisocyanate of general formula:

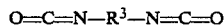

wherein $R^3$ is an alkylene, arylene or other bivalent organic residue of a diisocyanate, in a first anhydrous solvent;

(b) Preparing a solution of a polyurethane in a second anhydrous solvent;

(c) Thoroughly mixing the solutions obtained in (a) and (b);

(d) Desiccating the solution obtained in (c).

11. The process of claim 10, wherein the product obtained at the end of step (d) is a polyurethanic resin, cross-linked with copolymeric chains in correspondence of at least part of the urethane groups

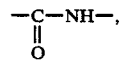

of said resin, as per the following general formula:

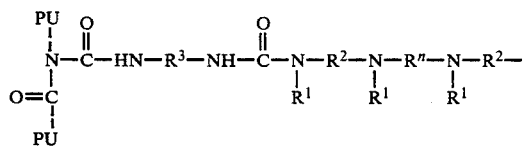

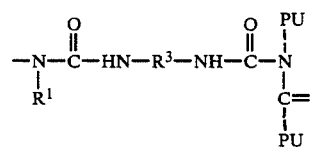

wherein, PU— is a polyurethanic polymeric chain, and $R^1$, $R^2$, $R^3$ and $R^n$ are as defined in claim 8.

12. The process of claim 10, wherein $R^n$ has the following general formula:

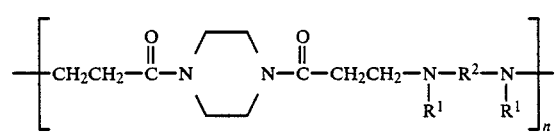

-continued

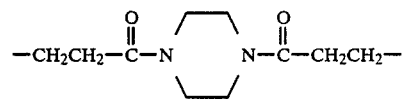

wherein $R^1$ and $R^2$ are as defined in claim 8 and n is at least one but low enough that the poly (amidoamine) precursor is soluble in an anhydrous organic solvent.

13. The process of claim 10, wherein:

$R^1$=—$CH_3$, $R^2$=—$(CH_2)_4$—, $R^3$=—$(CH_2)_6$—.

14. The process of claim 10, wherein said first solvent comprises methylene chloride, chloroform or dimethylsulphoxide.

15. The process of claim 10, wherein said second solvent comprises dimethylformamide, dimethylacetamide, or hexamethylphosphoramide.

16. The process of claim 10, wherein the molar ratio between diisocyanate and poly(amidoamine) is between 0.75:1 and 5:1.

17. The process of claim 10, wherein the molar ratio between polyurethane and poly(amidoamine) is between 100:1 and 1:1.

18. The process of claim 10, further comprising the step of submitting the product obtained at the end of the step (d) to a superficial heparinization treatment.

19. The process of claim 11 wherein $R^n$ has the following general formula:

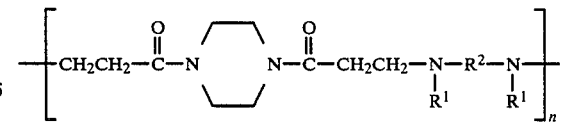

wherein $R^1$ and $R^2$ as are defined in claim 9 and n is at least one but low enough that the poly (amidoamine) precursor is soluble in an anhydrous organic solvent.

20. The process of claim 19 wherein $R^1$ is —$CH_3$, $R^2$ is —$(CH_2)_4$— and $R^3$ is —$(CH_2)_6$—.

21. The process of claim 12 wherein $R^1$ is —$CH_3$, $R^2$ is —$(CH_2)_4$— and $R^3$ is —$(CH_2)_6$—.

22. In a prosthetic element or medical equipment designed to come in contact with blood the improvement comprising at least partially constructing it from a synthetic material which has superficially adsorbed some heparin and which comprises a polyurethane resin crosslinked with copolymeric chains in correspondence of at least part of the urethane groups

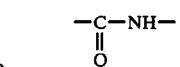

of said resin, as per the following general formula:

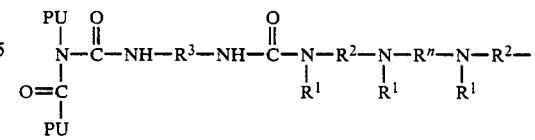

-continued
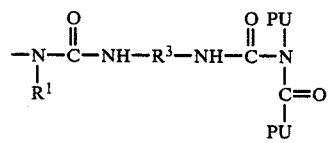
wherein
- PU—is a polyurethane polymeric chain;
- $R^1$ is an alkyl or aralkyl, containing no functional groups reactive with isocyanate;
- $R^2$ is an alkylene;
- $R^3$ is an alkylene, arylene or other bivalent organic residue of a diisocyanate; and
- $R^n$ is a polyamidoaminic radical.
* * * * *